(12) United States Patent
Kim et al.

(10) Patent No.: US 9,322,836 B2
(45) Date of Patent: Apr. 26, 2016

(54) BATCH CHEMICAL ANALYZER

(75) Inventors: Eun Hee Kim, Gyeonggi-do (KR); Kyoung Su Park, Gyeonggi-do (KR); Bum Joo Kang, Incheon (KR); Jae Gu Ahn, Incheon (KR); Song Beom Choi, Gyeonggi-do (KR); Ji Hyun Kwak, Seoul (KR); Hye Jin Won, Daegu (KR)

(73) Assignee: CENTENNIAL TECHNOLOGY COMPANY, Gyeonggi-Do (KR)

( * ) Notice: Subject to any disclaimer, the term of this patent is extended or adjusted under 35 U.S.C. 154(b) by 618 days.

(21) Appl. No.: 12/679,851

(22) PCT Filed: Feb. 13, 2009

(86) PCT No.: PCT/KR2009/000664
§ 371 (c)(1),
(2), (4) Date: Aug. 31, 2010

(87) PCT Pub. No.: WO2009/151198
PCT Pub. Date: Dec. 17, 2009

(65) Prior Publication Data
US 2011/0020180 A1 Jan. 27, 2011

(30) Foreign Application Priority Data
Jun. 12, 2008 (KR) .................. 10-2008-0055034

(51) Int. Cl.
G01N 30/02 (2006.01)
G01N 35/10 (2006.01)

(52) U.S. Cl.
CPC ................ *G01N 35/1097* (2013.01)

(58) Field of Classification Search
CPC ............. G01N 30/02; G01N 30/7233
USPC ............................ 422/70; 436/180
See application file for complete search history.

(56) References Cited

U.S. PATENT DOCUMENTS

| 5,413,686 A | 5/1995 | Klein et al. |
| 5,544,208 A * | 8/1996 | Pao et al. ............. 376/253 |
| 2002/0141900 A1* | 10/2002 | Guan et al. ............. 422/68.1 |
| 2007/0277596 A1* | 12/2007 | Kim et al. ............. 73/61.48 |

FOREIGN PATENT DOCUMENTS

| JP | 62-167482 | 7/1987 |
| KR | 10-2003-0064573 A | 8/2003 |

OTHER PUBLICATIONS

International Search Report in International Application No. PCT/KR2009/000664, filed Feb. 13, 2009.

* cited by examiner

*Primary Examiner* — Natalia Levkovich
(74) *Attorney, Agent, or Firm* — Saliwanchik, Lloyd & Eisenschenk

(57) ABSTRACT

A batch chemical analyzer is disclosed, the analyzer including a reaction tank (100) in which sample and reagent are mixed, a detector (200), a switching valve (300), a multi-port valve (400), a pump (500) and an air suction/discharge hole (600), and particularly, the switching valve (300) includes a plurality of holes (301~310) configured to receive sample and reagent and to send the same to the reaction tank (100) and the detector (200) for discharge to the outside, and the rotor (320) formed with a plurality of inlets (321~325) simultaneously communicating with two adjacent holes of the plurality of holes (301~310), whereby the two adjacent holes are differently paired to be communicated in two ways by the rotation of the rotor (320).

1 Claim, 8 Drawing Sheets (a)　　　　　　　(b)　　　　　　　(c)

BATCH CHEMICAL ANALYZER

DETAILED DESCRIPTION OF THE INVENTION

1. Technical Field

The present invention relates to a chemical analyzer configured to automatically analyze a liquefied sample, and more particularly to a batch chemical analyzer configured to solve the problem of foreign substances being accumulated in a multi-port valve introducing samples and reagents by repeatedly circulating the samples and reagents in the conventional closed loop.

2. Background

Generally, an automatic chemical analyzer is an apparatus for analyzing liquefied sample in a hospital testing room, and agricultural, medical, chemical and environment fields, and have been developed in various ways in order to automatically process a large amount of samples within a short period of time, and to enhance reproducibility and accuracy of analytical assays.

The conventional automatic chemical analysis may be largely categorized into three types based on the analyzing method, that is, a batch analysis that individually separates and analyzes samples one by one, a segment flow analysis (SFA) that injects air bubbles at a predetermined interval into a liquid continuously flowing in a glass tube, and a flow injection analysis (FIA) that instantly injects samples without injecting air bubbles into a continuously-flowing liquid.

The SFA and FIA suffer from disadvantages in that a reaction time is restrained and it is difficult to implement an entire pre-treatment process such as a high temperature heating in a continuous flow. Although the SFA has a maximum reaction time of 20 minutes, the FIA usually has a reaction time of 1 minute and under. The maximum heating temperature in SFA is 95□ while that of FIA is in the range of 60□.

The SFA and FIA that employ a continuous flow analyzing method suffer from another disadvantage in that it is difficult to analyze samples containing lots of particulate matters, and particularly, the reliability of analysis result decreases if air bubbles are generated in a tube due to temperature or pressure changes in the samples, and more particularly, detectors in the FIA tend to make errors if air bubbles are generated due to increased pressure in a tube, because solution is transferred in a tube having an internal diameter of 0.8□1 mm at the rate of 2□4 ml per minute.

The batch analysis employs a method in which the sample is manually inserted into a vessel and the reagent is sequentially poured for analysis, and is mainly used as an on-line analytic apparatus for field installation due to its stability. However, the batch analysis suffers from disadvantages in that many driving parts including valves, pumps and detectors are needed to complicate the apparatus and to increase failure rates, thereby increasing the manufacturing cost.

The following reference is found to be pertinent to the field of the present invention: Korea Pat. No. 10-449188 disclosed a micro-batch chemical analyzer.

The micro-batch chemical analyzer includes a loop tube (1) in which fluid flows, a multi-port valve (10) formed with a plurality of outlets (11) mounted on a fluid path of the loop tube (1) for introducing fluid or air into the loop tube (1) or discharging fluid or air from the loop tube (1), a bi-directional pump (20) for sucking, discharging the fluid or air or rotating the fluid or air inside the loop tube (1) for mixture thereof, a detector (30) configured to measure a reaction status of a sample, a reactor or reaction tank (40) configured to mix the solution to generate a chemical reaction, and a valve (60) configured to change the fluid path.

The micro-batch chemical analyzer has many advantages of minimized reagent consumption, a smooth performance of complete unmanned automatic analysis with minimized energy consumption and of component analysis of samples in various methods after pre-treatment process, and measurement of samples in a broad concentration range by diluting and concentrating the samples.

However, the micro-batch chemical analyzer according to the Korea Patent No.: 10-449188 has a disadvantage in that the multi-port valve (10), the bi-directional pump (20), the detector (30), the reactor or reaction tank (40) and the valve (60) must be all connected to one loop tube (1). As a result, in a case a sample containing a highly concentrated particulate matter is to be analyzed, foreign substances are accumulated in holes of a multi-port valve (400) due to repeated circulation of samples and reagents in a closed loop after the samples and reagents are mixed to clog the holes of the valve. Another disadvantage is that designing of various products is limited due to connection of all components to one loop tube (1).

CONTENTS OF THE INVENTION

Technical Subject

Accordingly, it is an object of the present invention to provide a batch chemical analyzer configured to connect a multi-port valve capable of introducing samples and reagents from outside to a loop tube separately from other components and to dispense with connection of various components such as a reaction tank, a detector and a multi-port valve to one closed loop tube, whereby a problem can be solved in which foreign substances are accumulated in holes of the multi-port valve due to repeated circulation of samples and reagents in the closed loop after the samples and reagents are mixed to clog the holes of the valve, and it is possible to design various products.

Technical Solution

According to one general aspect of the present invention, there is provided a batch chemical analyzer, comprising: a reactor or reaction tank (100) configured to mix a sample and a reagent; a detector (200) configured to detect a reaction status of the sample and reagent; a switching valve (300) formed with a plurality of holes (301□310) configured to receive the sample and the reagent for transfer to the reaction tank (100) and the detector (200), and circulation of the sample and the reagent in the holes, and a rotor (320) formed with a plurality of inlets (321□325) simultaneously corresponding to two adjacent holes out of the plurality of holes, wherein the two adjacent holes are communicated in a different pair by the rotation of the rotor (320) in two cases; a multi-port valve (400) radially formed with a plurality of inlets/outlets (410) and selectively communicating any one or more inlets/outlets (410) out of the inlets/outlets to allow selectively supplying the sample and the reagent from the outside; a pump (500) configured to transfer to the switching valve (300) one or more of the sample and the reagent supplied from the multi-port valve (400); and an air suction/discharge hole (600) configured to circulate the sample and the reagent to the reaction tank (100) and the detector (200) and to supply air to one of the plurality of holes (301□310) of the switching valve (300) for discharge to the outside, wherein the two adjacent holes of the switching valve (300) communicating by way of two cases includes a first case in which the pump (500) and the reaction tank (100) are interconnected to allow the two adjacent holes (308, 307) to communicate, and a second case in which two holes (306, 307) adjacent by way of connecting the air suction/discharge hole (600) and the reaction tank (100), and two holes (301, 310) adjacent by way of connecting the reaction tank (100) and the detector (200) are simultaneously communicated.

In some exemplary embodiments, the second case is preferably configured in such a manner that two adjacent holes (308, 309) connected to the detector (200) and the pump (500) are simultaneously communicated, and the pump (500) and the multi-port valve (400) discharge the air transferred from the detector (200) to the outside through the multi-port valve (400).

According to another general aspect of the present invention, there is provided a batch chemical analyzer, comprising: a reactor or reaction tank (100) configured to mix a sample and a reagent; a detector (200) configured to detect a reaction status of the sample and reagent; a switching valve (300) formed with a plurality of holes (301☐310) configured to receive the sample and the reagent for transfer to the reaction tank (100) and the detector (200), and circulation of the sample and the reagent in the holes, and a rotor (320) formed with a plurality of inlets (321☐325) simultaneously corresponding to two adjacent holes out of the plurality of holes, wherein the two adjacent holes are communicated in a different pair by the rotation of the rotor (320) in two cases; a multi-port valve (400) radially formed with a plurality of inlets/outlets (410) and selectively communicating any one or more inlets/outlets (410) out of the inlets/outlets to allow selectively supplying the sample and the reagent from the outside; a pump (500) configured to transfer to the switching valve (300) one or more of the sample and the reagent supplied from the multi-port valve (400); and an air suction/discharge hole (600) configured to circulate the sample and the reagent to the reaction tank (100) and the detector (200) and to supply air to one of the plurality of holes (301☐310) of the switching valve (300) for discharge to the outside, wherein the batch chemical analyzer may further comprise: connecting pipes (7, 8) connecting two adjacent holes (307, 308) out of plurality of holes (301~310) of the switching valve (300) with the reaction tank (100) and the pump (500); a connecting pipe (6) connecting another hole (306) adjacent to the hole (307) connected to the reaction tank (100) with the air suction/discharge hole (600); and connecting pipes (1, 10) connecting two adjacent holes (301, 310) in addition to the holes (307, 308, 306) connected to the reaction tank (100), the pump (500) and the air suction/discharge hole (600) with the reaction tank (100) and the detector (200).

In some exemplary embodiments, the batch chemical analyzer may further comprise a connecting pipe (9) connecting the detector (200) to said another hole (309) adjacent to the hole (308) connected to the pump (500).

According to still another general aspect of the present invention, there is provided a batch chemical analyzer, comprising: a reactor or reaction tank (100) configured to mix a sample and a reagent; a detector (200) configured to detect a reaction status of the sample and reagent; a switching valve (300) formed with a plurality of holes (301☐310) configured to receive the sample and the reagent for transfer to the reaction tank (100) and the detector (200), and circulation of the sample and the reagent in the holes, and a rotor (320) formed with a plurality of inlets (321☐325) simultaneously corresponding to two adjacent holes out of the plurality of holes, wherein the two adjacent holes are communicated in a different pair by the rotation of the rotor (320) in two cases; a multi-port valve (400) radially formed with a plurality of inlets/outlets (410) and selectively communicating any one or more inlets/outlets (410) out of the inlets/outlets to allow selectively supplying the sample and the reagent from the outside; a pump (500) configured to transfer to the switching valve (300) one or more of the sample and the reagent supplied from the multi-port valve (400); and an air suction/discharge hole (600) configured to circulate the sample and the reagent to the reaction tank (100) and the detector (200) and to supply air to one of the plurality of holes (301☐310) of the switching valve (300) for discharge to the outside, wherein the first hole (301) of the switching valve (300) is connected to the reaction tank (100) to communicate with the tenth hole (310) connected to the detector (200), the second hole (302) is communicated to the third hole (303) connected to the reaction tank (100), the fourth hole (304) is communicated to the fifth hole (305) connected to the reaction tank (100) but is closed, the sixth hole (306) is connected to the air suction/discharge hole (600) to communicate with the seventh hole (307) connected to the reaction tank (100), the seventh hole (307) communicates with the sixth hole (306) or communicates with the eighth hole (308) connected to the pump (500), the eighth hole (308) communicates with the seventh hole (307) or communicates with the ninth hole (309) connected to the detector (200).

In some exemplary embodiments, the rotor (320) of the switching valve (300) preferably rotates by being communicated in two selective cases by allowing said two adjacent holes are paired in a different manner, and rotates by allowing one inlet out of the plurality of inlets (321☐325) to be brought into contact with one hole out of the plurality of holes (301~310).

In some exemplary embodiments, the detector (200) may include two or more detectors, wherein the two or more detectors may detect mutually different substances.

Other details of the exemplary embodiments will be described with reference to the Detailed Description and accompanying drawings.

Advantageous Effect

The advantages of the present invention lie in the fact that the batch chemical analyzer is configured to connect a multi-port valve capable of introducing samples and reagents from outside to a loop tube separately from other components and to dispense with connection of various components such as a reaction tank, a detector and a multi-port valve to one closed loop tube, whereby a problem can be solved in which foreign substances are accumulated in holes of the multi-port valve due to repeated circulation of samples and reagents in the closed loop after the samples and reagents are mixed to clog the holes of the valve, and it is possible to design various products.

BEST MODES

The present invention will be described more fully hereinafter with reference to the accompanying drawings, in which exemplary embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art.

FIG. 1 is a front view illustrating a schematic configuration of a batch chemical analyzer according to an exemplary embodiment of the present invention.

Referring to FIG. 1, the batch chemical analyzer according to the present invention includes a reaction tank (100) configured to mix a sample and a reagent; a detector (200) configured to detect a reaction status of the sample and reagent; a switching valve (300) configured to receive the sample and the reagent for dispatch to the reaction tank (100) and the detector (200) and for discharge to the outside; a multi-port valve (400) configured to selectively receiving the sample and the reagent from the outside; a pump (500) transferring the sample and the reagent supplied from the multi-port valve (400) to the switching valve (300); and an air suction/discharge hole (600) in which air is communicated to the switching valve (300) for circulation and discharge of the sample and the reagent.

The reaction tank (100), the detector (200), the multi-port valve (400) and the pump (500) are connected to a plurality of holes of the switching valve (300), and particularly, one of the plurality of holes of the switching valve (300) is connected to the air suction/discharge hole (600), and two adjacent holes of the switching valve (300) are differently paired to allow the air to be sucked and discharged in two selective ways.

The present invention is to connect a multi-port valve capable of introducing samples and reagents from outside to a loop tube separately from other components and to dispense with connection of various components such as a reaction tank, a detector and a multi-port valve to one closed loop tube, whereby a problem can be solved in which foreign substances are accumulated in holes of the multi-port valve due to repeated circulation of samples and reagents in the closed loop after the samples and reagents are mixed to clog the holes of the valve, and it is possible to design various products.

First of all, the reaction tank (100) is a chamber for mixing the sample and the reagent therein. The sample and the reagent are supplied from the outside, where the sample and the reagent are transferred to the switching valve (300) by the pump (500) via the multi-port valve (400) to be introduced into the reaction tank (100) through a pipe formed at an upper end of the reaction tank (100). The sample and the reagent may be selectively introduced to the reaction tank (100), one by one and kind by kind, by the plurality of inlets/outlets formed at the multi-port valve (400).

The reaction tank (100) may be made of pyrex (a brand name by Corning of US) glass to have an excellent shock-resistance and an excellent chemical durability, where the reaction tank (100) may further include a heater (not shown) configured to heat the reaction tank (100) at a predetermined temperature by attaching a temperature sensor and a silicon rubber heater therearound and an agitator (not shown) configured to agitate inside the reaction tank (100).

Furthermore, the detector (200) is configured to detect and analyze the reaction status of sample and reagent. An object, a method and a configuration covered by the detector are not limited. For example, the detector (200) may include a flow cell for passing liquid, a light source and a detecting sensor. The detector (200) may measure suction of light or fluorescence based on wavelength of light when liquid (sample and reagent) passes, and may detect particular substances with an electrochemical sensor that is attached thereon.

The switching valve (300) receives the liquid (sample and reagent) from the multi-port valve (400) via the pump (500) and allows the liquid to be transmitted to and circulated in the reaction tank (100) and the detector (200). Upon completion of analysis in the detector (200), the liquid is discharged to the outside.

FIG. 2 is a perspective view illustrating an exemplary structure of a switching valve (300) according to the present invention.

Referring to FIG. 2, the switching valve (300) may include a plurality of holes (301~310) and a rotor (320) formed with a plurality of inlets/outlets (321~325) simultaneously corresponding to two adjacent holes among the plurality of holes (301~310). Therefore, as shown in FIG. 3, the present invention has the feature in which two adjacent holes are differently paired by the rotation of the rotor (320) and communicated in two selective cases.

That is, FIG. 3 is a mimetic diagram illustrating an operation and function of a switching valve (300) according to the present invention.

Referring to FIG. 3, two adjacent holes out of the plurality of holes (301~310) are differently paired and communicated in two selective cases by the rotation of the rotor (320) formed with the plurality of inlets/outlets (321~325), where the first case is such that two adjacent holes (301, 310) are paired and communicated as shown in FIG. 3(a), and the second case is such that two adjacent holes (301, 302) are paired and communicated as depicted in FIG. 3(b). The third case of FIG. 3(c) is such that no holes (301~310) of the switching valve (300) are mutually communicated, which will be described later.

Furthermore, the multi-port valve (400) selectively receives one or more of the sample and the reagent from the outside. FIG. 4 is a perspective view illustrating an exemplary structure of a multi-port valve (400) according to the present invention.

The multi-port valve (400) is radially formed with a plurality of outlets (410) and selectively communicates one or more of the outlets (410). That is, FIG. 5 is a mimetic diagram illustrating an operation and function of a multi-port valve according to the present invention.

As depicted in FIG. 5, the sample and the reagent are selectively supplied as the inlet formed at the rotor communicates with one or more outlets. The pump (500) serves to transport one or more of the sample and the reagent supplied from the multi-port valve (400) to the switching valve (300). That is, the sample and the reagent are quantitatively fed to the switching valve (300) according to rotation and vertical movement of a ceramic piston.

Furthermore, in the present invention, an air suction/discharge hole (600) is connected to the switching valve (300). The air is sucked in or discharged out through one of the holes (301, 310) of the switching valve (300), whereby the liquid (the sample and the reagent) transferred to the switching valve (300) are sent to the reaction tank (100) and the detector (200), where the liquid is circulated therein and discharged out thereafter.

The present invention relates to a batch chemical analyzer configured to automatically analyze a liquefied sample. Hereinafter an actual process of chemically analyzing samples will be described in detail with reference to the accompanying drawings.

In order to analyze the sample using the batch chemical analyzer according to the present invention, the analyzing method may at least have to go through: collecting a sample (S100); pouring the sample (S200); and circulating the sample and a reagent using a detector and measuring an absorbance (S300).

Alternatively, the method may further include measuring (S110) an initial luminous intensity for correction of turbidity of sample following the collection of sample (S100), or cooling the sample (S130) after pressing and heating the sample (S120) for easy oxidation. The method may further include discharging the measured and wasted sample and reagent (S310) after measurement of absorbance.

FIG. 6 is a mimetic diagram illustrating a process (S100) in which a sample is poured in a batch chemical analyzer according to an exemplary embodiment of the present invention.

To this end, it is essential that each of the outlets (410) formed at the multi-port valve (400) be connected to a sample liquid containing at least one or more samples. It should be also apparent that each of the outlets may be connected to various sample liquids.

In order to introduce the sample, the first case may be set up in which the switching valve (300) is connected to the pump (500) and the reaction tank (100) to allow two adjacent holes (308, 307) to communicate each other {see FIG. 3 (*b*)}.

That is, one hole (308) of the switching valve (300) connected to the pump (500) is communicated with another hole (307) connected to the reaction tank (100) by the rotation of the rotor (320) formed at the switching valve (300). Then, the pump (500) may transport the sample supplied from the multi-port valve (400) to the reaction tank (100) via the two adjacent holes (308, 307). At this time, the air existing in the reaction tank (100) is discharged to the outside of the reaction tank via the air suction/discharge hole (600) according to introduction of sample.

As noted above, the switching valve (300) basically serves to transport the sample from the pump (500) to the reaction tank (100), and to this end, the switching valve (300) is preferably formed with a predetermined connection pipe. For example, the switching valve (300) may be formed with connection pipes (7, 8) configured to connect the reaction tank (100) and the pump (500) with the two adjacent holes (307, 308) out of the plurality of holes (301~310) of the switching valve (300) according to another exemplary embodiment of the present invention. In this case, the sample supplied from the multi-port valve (400) may be transferred to the reaction tank (100) through the communicated two adjacent holes (308, 307).

The processing steps according to the present invention may further include measuring (S110) an initial luminous intensity for correction of turbidity of sample following the collection of sample (S100), and cooling the sample (S130) after pressing and heating the sample (S120) for easy oxidation. The step of measuring of the initial luminous intensity of the sample (S110) is to correct the turbidity/chromaticity of the sample based on a result of a later measurement by measuring the initial luminous intensity by sending the sample introduced to the reaction tank (100) to the detector (200) prior to mixing the sample with the reagent.

Furthermore, the step of pressing and heating the sample (S120) includes the steps of pouring the sample into the reaction tank (100), introducing an oxidant as a pre-treatment reagent (the pouring of pre-treatment reagent is the same as the pouring of sample or reagent), disengaging the reaction tank (100) from the outside and pressing and heating the sample, which is to promote a faster oxidation of the pre-treatment reagent.

FIG. 7 is a mimetic diagram illustrating a status in which a reaction tank is pressed and heated in a batch chemical analyzer according to an exemplary embodiment of the present invention.

Referring to FIG. 7, in order to press and heat the reaction tank (100), it is essential that air vents of the reaction tank (100) be blocked. To this end, the rotor (320) formed at the switching valve (300) is rotated in such a manner that one inlet out of the plurality of inlets (321~325) is brought into contact with only one hole out of the plurality of holes (301~310) {see FIG. 3(*c*)}. That is, no holes (301~310) of the switching valve (300) are allowed to be communicated by the rotation of the rotor (320).

According to the present invention, the rotor (320) of the switching valve (300) is rotated in two ways, where the first way is that the two adjacent holes are differently paired to be communicated in two cases, and the other way is that one inlet of the plurality of inlets (321~325) is brought into contact with only one of the holes (301~310), whereby the reaction tank (100) can be blocked from the outside to enable an easy pressing and heating the sample containing pre-treatment reagent. Thereafter, a process is performed where the reaction tank (100) is cooled, and vents of the reaction tank (100) are opened (S130).

Next, FIG. 8 is a mimetic diagram illustrating a status in which a sample is poured in a batch chemical analyzer according to an exemplary embodiment of the present invention.

The pouring of the sample (S200) can be easily performed by selectively communicating a plurality of outlets (410) of the multi-port valve (400) as in the above process of introducing the sample.

FIG. 9 is a mimetic diagram illustrating a status in which a sample and a reagent are transferred (S300) to a detector in a batch chemical analyzer according to an exemplary embodiment of the present invention.

Referring to FIG. 9, in order to transfer the sample and the reagent to the detector (200), the switching valve (300) may be set up in the second case {see FIG. 3(*a*)}, where two adjacent holes (306, 307) connected to the air suction/discharge hole (600) and the reaction tank (100) and the two adjacent holes (301, 310) connected to the reaction tank (100) and the detector (200) are simultaneously communicated.

That is, one hole (306) of the switching valve (300) connected to the air suction/discharge hole (600) and another hole (307) connected to the reaction tank (100) are mutually communicated by rotation of the rotor (320) formed at the switching valve (300), and simultaneously, still another hole (301) of the switching valve (300) connected to the reaction tank (100) and still further another hole (310) connected to the detector (200) are mutually communicated. Then, the switching valve (300) can transfer the sample and the reagent in the reaction tank (100) to the detector (200) via the two communicated pairs (306, 307) (301, 310).

As noted above, the switching valve (300) basically serves to transport the sample and the reagent from the reaction tank (100) to the pump (500), and to this end, the switching valve (300) is preferably formed with a predetermined connection pipe. For example, the switching valve (300) may be further formed with a connection pipe (6) configured to connect the another hole (306) adjacent to the hole (307) connected to the reaction tank (100) to the air suction/discharge hole (600) and connection pipes (1, 10) connecting the reaction tank (100) and the detector (200) to the two adjacent holes (301, 310) in addition to the holes (307, 308, 306) connected to the reaction tank (100), the pump (500) and the air suction/discharge hole (600), according to still another exemplary embodiment of the present invention. In this case, the batch chemical analyzer (particularly the switching valve 300) can transfer the sample and the reagent in the reaction tank (100) to the detector (200) through the communicated two paired holes (306, 307) (301, 310).

In the present invention, the transfer of the sample and the reagent from the reaction tank (100) to the detector (200) can be implemented because the air supplied from the air suction/discharge hole (600) moves through one hole (306, 307) of the switching valve (300), the reaction tank (100), the other hole (301, 310) of the switching valve (300) and the detector (200). Furthermore, the air, the sample and the reagent that have reached the detector (200) may be discharged from the detector (200). Furthermore, the present invention may be further formed with another hole (309) adjacent to the hole (308) connected to the pump (500), and the connection pipe (9) configured to connect the detector (200), whereby the sample, the air and the reagent that have reached the detector (200) are continuously moved to the pump (500) and the multi-port valve (400).

More preferably, only the air that has reached the detector (200) may be transported to the pump (500) and the multi-port valve (400). The present invention may have an effect of removing foreign substances inside the pump (500) and the multi-port valve (400) along with the smooth circulation of the sample and the reagent using the transported air.

That is, in the second case where two adjacent holes of the switching valve (300) are communicated in two ways, it is preferable that the two adjacent holes (308, 309) connected to the detector (200) and the pump (500) be simultaneously communicated, and the pump (500) and the multi-port valve (400) discharge the air transported from the detector (200) to the outside through the multi-port valve (400).

Once the sample and the reagent are transported to the detector (200), the detector (200) detects and analyzes the sample and the reagent. If the sample and the reagent have been all transported from the reaction tank (100), there is no need of discharging the sample and the reagent separately. However, some of the sample and the reagent remain in the reaction tank (100), although the sample and the reagent have been transported to the reaction tank (100) following the detection, the present invention may further include a process (S310) of discharging the wasted liquid in which the remaining sample is discharged to the outside in order to analyze other samples.

FIG. 10 is a mimetic diagram illustrating a process (S310) in which a sample and a reagent are discharged to the outside in a batch chemical analyzer according to an exemplary embodiment of the present invention.

Referring to FIG. 10, the sample and reagent remaining in the reaction tank (100) may be discharged to the outside from a lower section of the reaction tank (100) via the communicated holes (302, 303) of the switching valve (300) by the air supplied to the reaction tank (100) through the air suction/discharge hole (600). The discharge outlet may be formed with a separate pump (not shown) to promote the discharge of the wasted liquid.

As noted from the foregoing, the batch chemical analyzer according to the present invention includes a reaction tank (100) in which sample and reagent are mixed, a detector (200), a switching valve (300), a multi-port valve (400), a pump (500) and an air suction/discharge hole (600), and particularly, the switching valve (300) includes a plurality of holes (301~310) configured to receive sample and reagent and to send the same to the reaction tank (100) and the detector (200) for discharge to the outside, and the rotor (320) formed with a plurality of inlets (321~325) simultaneously communicating with two adjacent holes of the plurality of holes (301~310), whereby the two adjacent holes are differently paired to be communicated in two ways by the rotation of the rotor (320).

Furthermore, instead of connecting and fixing the multi-port valve (400) introducing the sample and the reagent from the outside to one loop pipe, the multi-port valve (400) is connected in a separate configuration to solve the disadvantage of the foreign substances being collected inside a hole of the multi-port valve (400) by the repeated circulation of the sample and the reagent, unlike the conventional analyzer.

To be more specific, as illustrated in FIGS. 6 to 10, the first hole (301) of the switching valve (300) is connected to the reaction tank (100) to communicate with the tenth hole (310) connected to the detector (200), the second hole (302) is connected to the third hole (303) connected to the reaction tank (100), the fourth hole (304) is connected to the fifth hole (305) connected to the reaction tank (100) but is closed, the sixth hole (306) is connected to the air suction/discharge hole (600) to communicate with the seventh hole (307) connected to the reaction tank (100), the seventh hole (307) communicates with the sixth hole (306) or communicates with the eighth hole (308) connected to the pump (500), the eighth hole (308) communicates with the seventh hole (307) or communicates with the ninth hole (309) connected to the detector (200), whereby the present invention can obtain the advantages and effect.

It should be also apparent that the batch chemical analyzer may include two or more detectors (200) configured to detect mutually different substances whereby various substances can be simultaneously or sequentially detected. That is, two or more detectors (200) may be connected in series or in parallel on a single path to measure various substances simultaneously or sequentially.

Although embodiments have been described with reference to a number of illustrative embodiments thereof, it should be understood that numerous other modifications and embodiments can be devised by those skilled in the art that will fall within the spirit and scope of the principles of this disclosure. More particularly, various variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

As noted, the batch chemical analyzer has an industrial applicability in that it can solve the problem of foreign substances being accumulated in a hole of a multi-port valve receiving samples and reagents from outside by repeatedly circulating the samples and reagents, and it is possible to manufacture products of various designs.

BRIEF DESCRIPTION OF THE DRAWINGS

The accompanying drawings, which are included to provide a further understanding of the invention and are incorporated in and constitute a part of this application, illustrate embodiment(s) of the invention, and together with the description serve to explain the principle of the invention. In the drawings.

Figure 1:
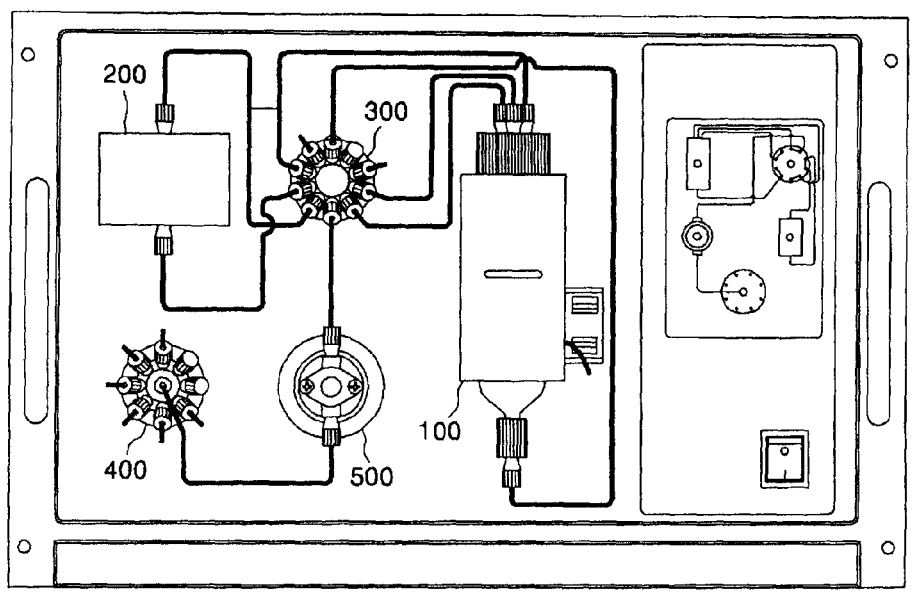
FIG. 1 is a front view illustrating a schematic configuration of a batch chemical analyzer according to an exemplary embodiment of the present invention.
Figure 2:
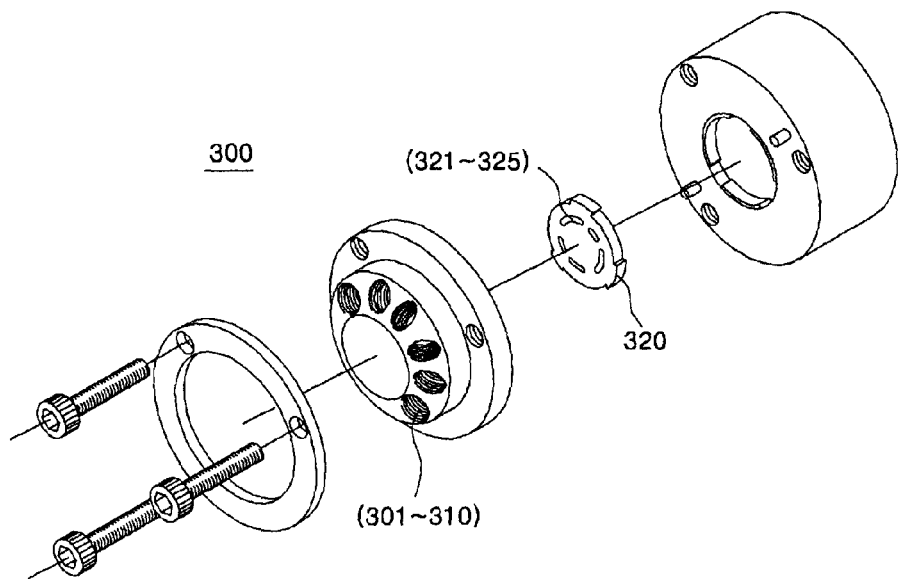
FIG. 2 is a perspective view illustrating an exemplary structure of a switching valve according to the present invention.
Figure 3:
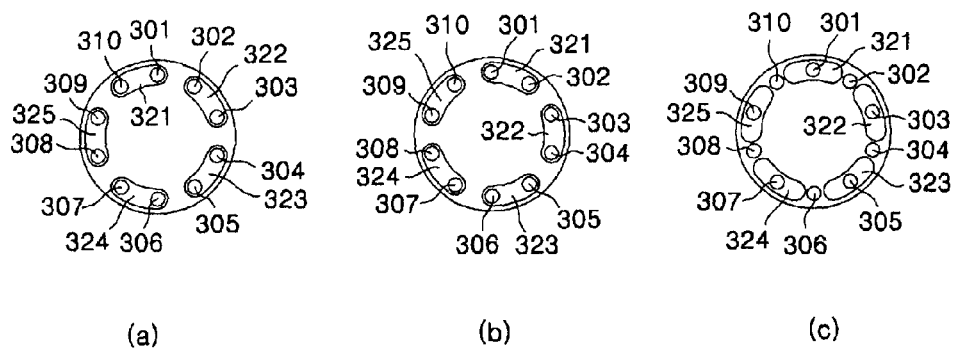
FIG. 3 is a mimetic diagram illustrating an operation and function of a switching valve according to the present invention.
Figure 4:
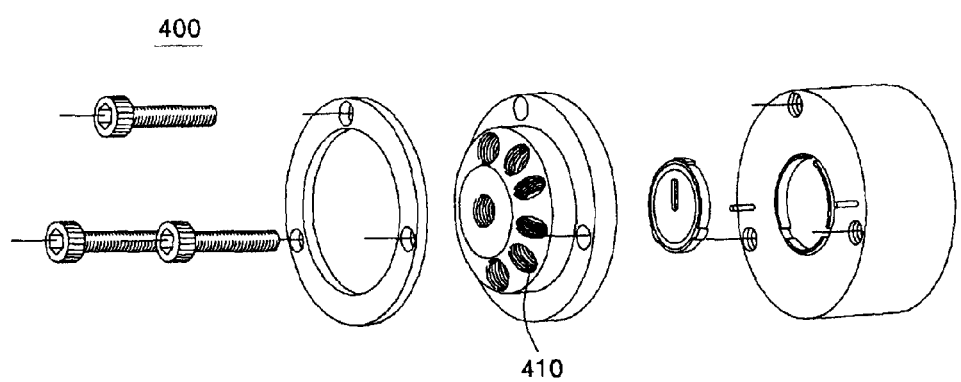
FIG. 4 is a perspective view illustrating an exemplary structure of a multi-port valve according to the present invention.
Figure 5:
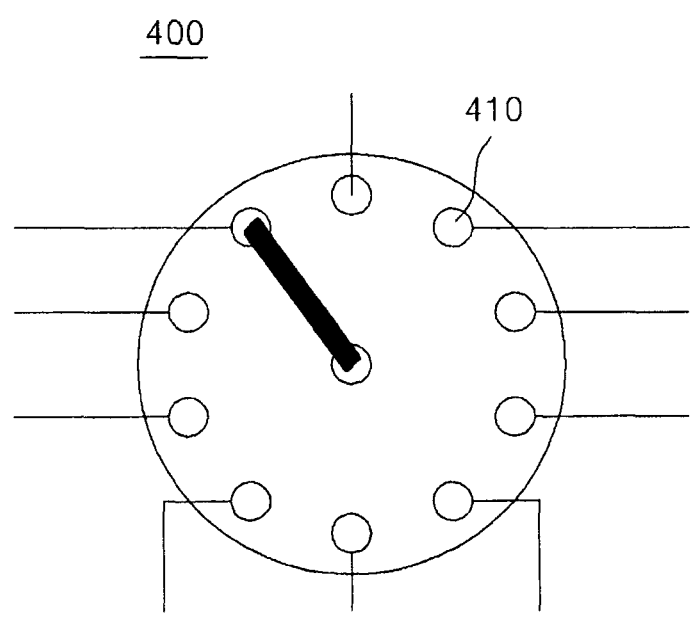
FIG. 5 is a mimetic diagram illustrating an operation and function of a multi-port valve according to the present invention.
Figure 6:
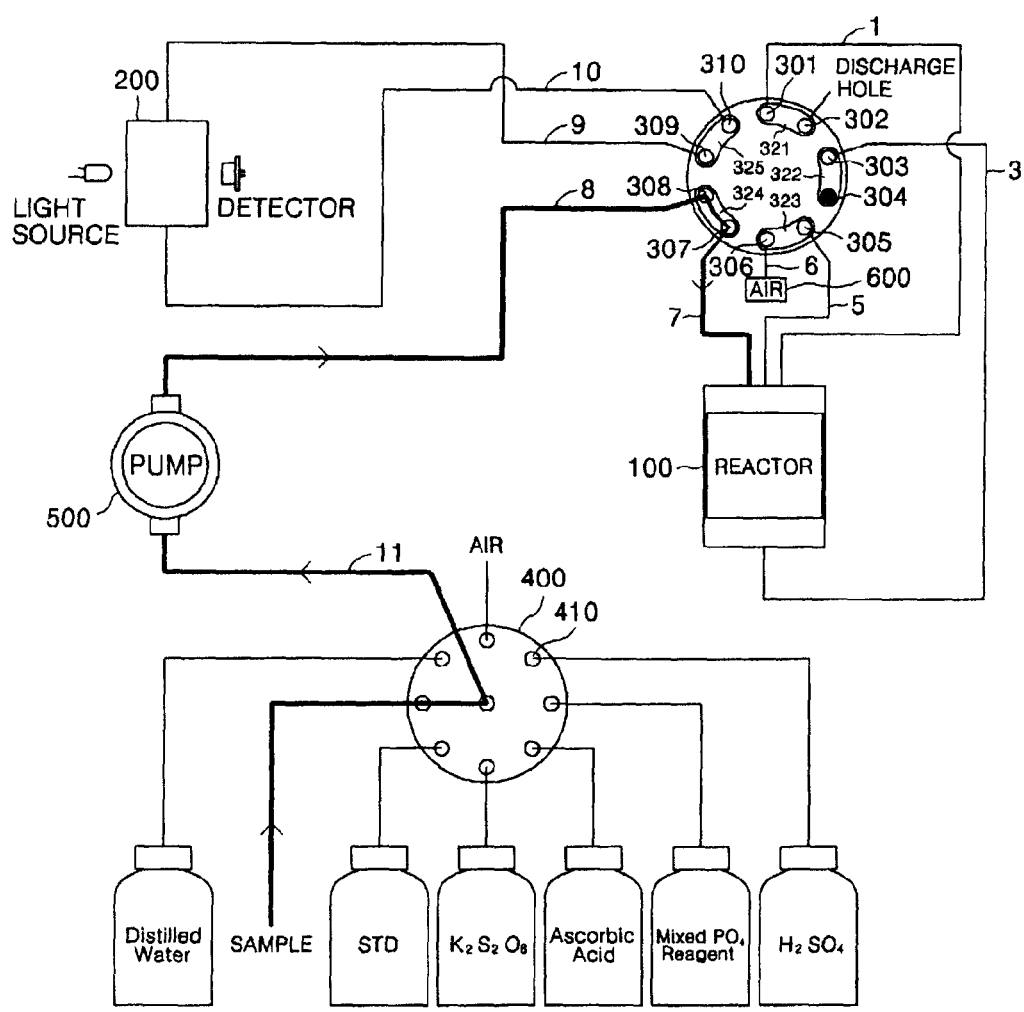
FIG. 6 is a mimetic diagram illustrating a status in which a sample is poured in a batch chemical analyzer according to an exemplary embodiment of the present invention.
Figure 7:
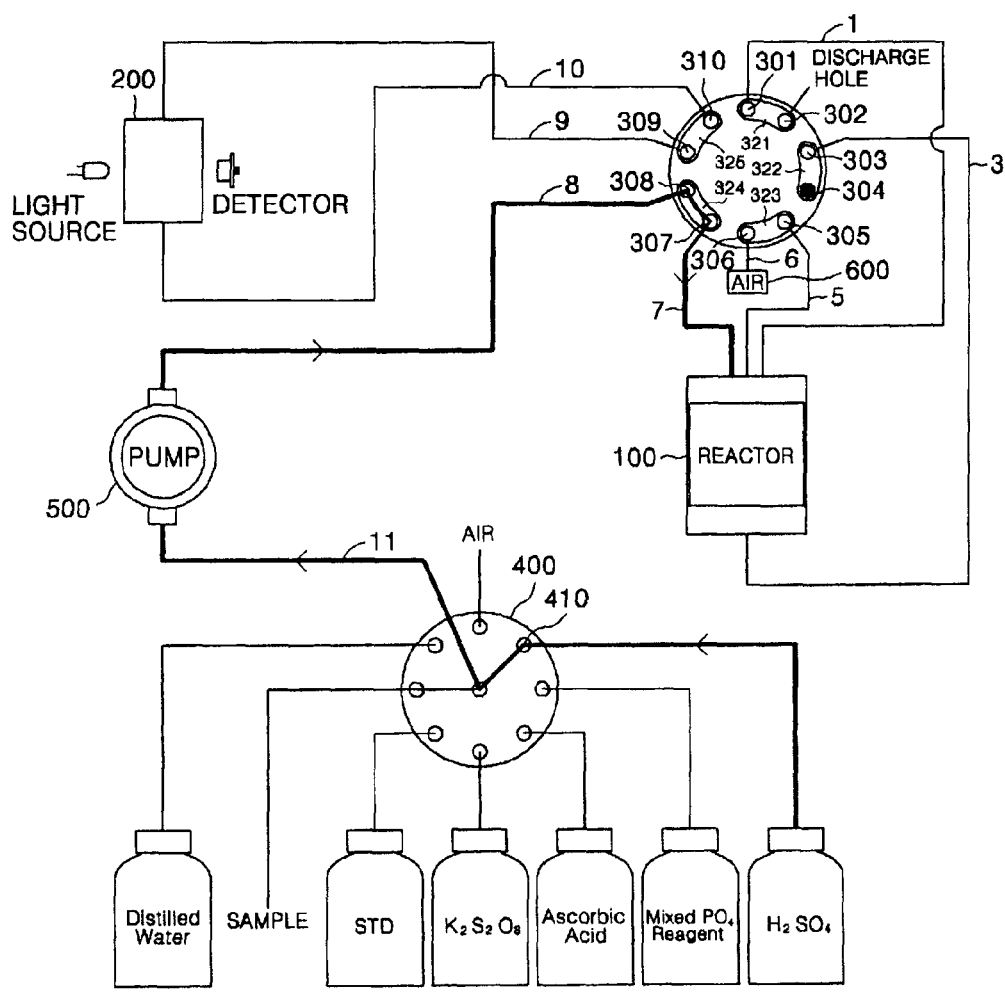
FIG. 7 is a mimetic diagram illustrating a status in which a reaction tank is pressed and heated in a batch chemical analyzer according to an exemplary embodiment of the present invention.
Figure 8:
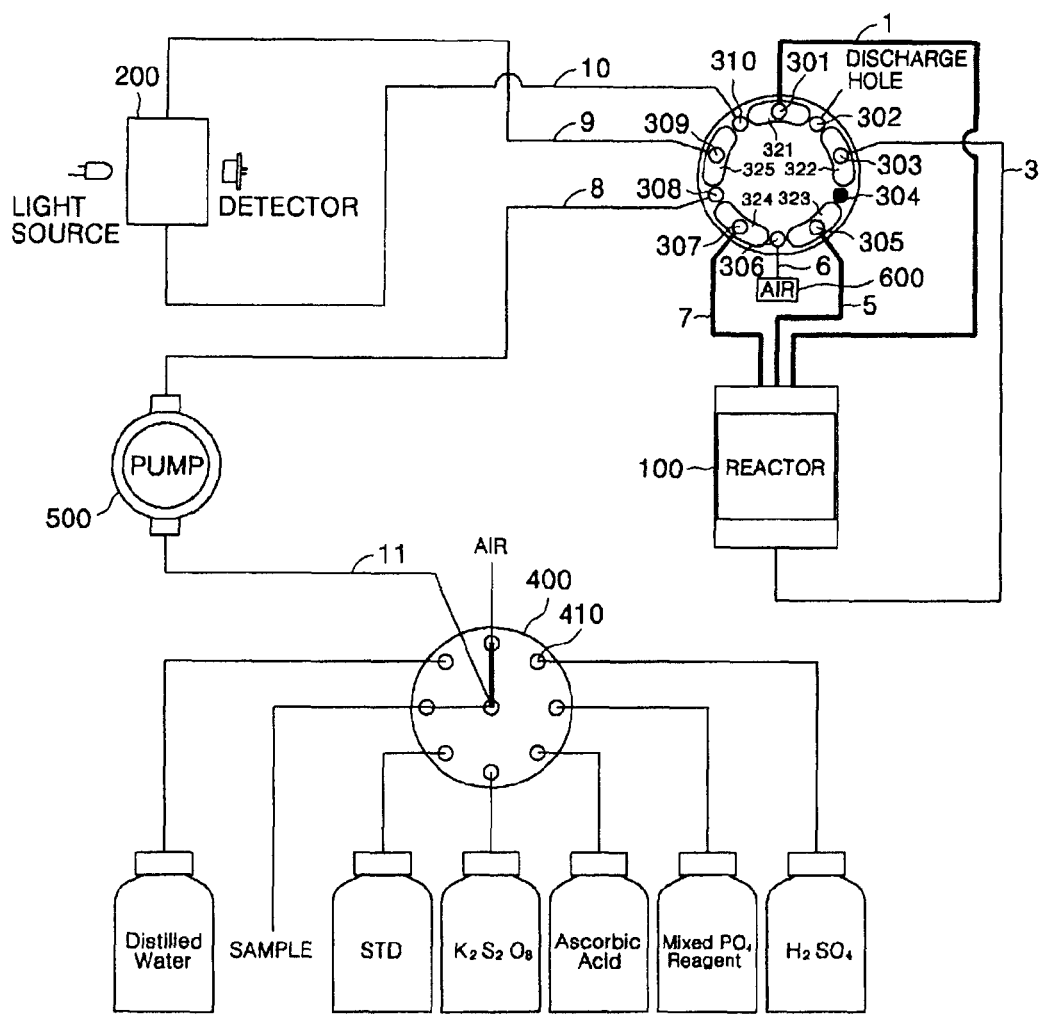
FIG. 8 is a mimetic diagram illustrating a status in which a sample is poured in a batch chemical analyzer according to an exemplary embodiment of the present invention.
Figure 9:
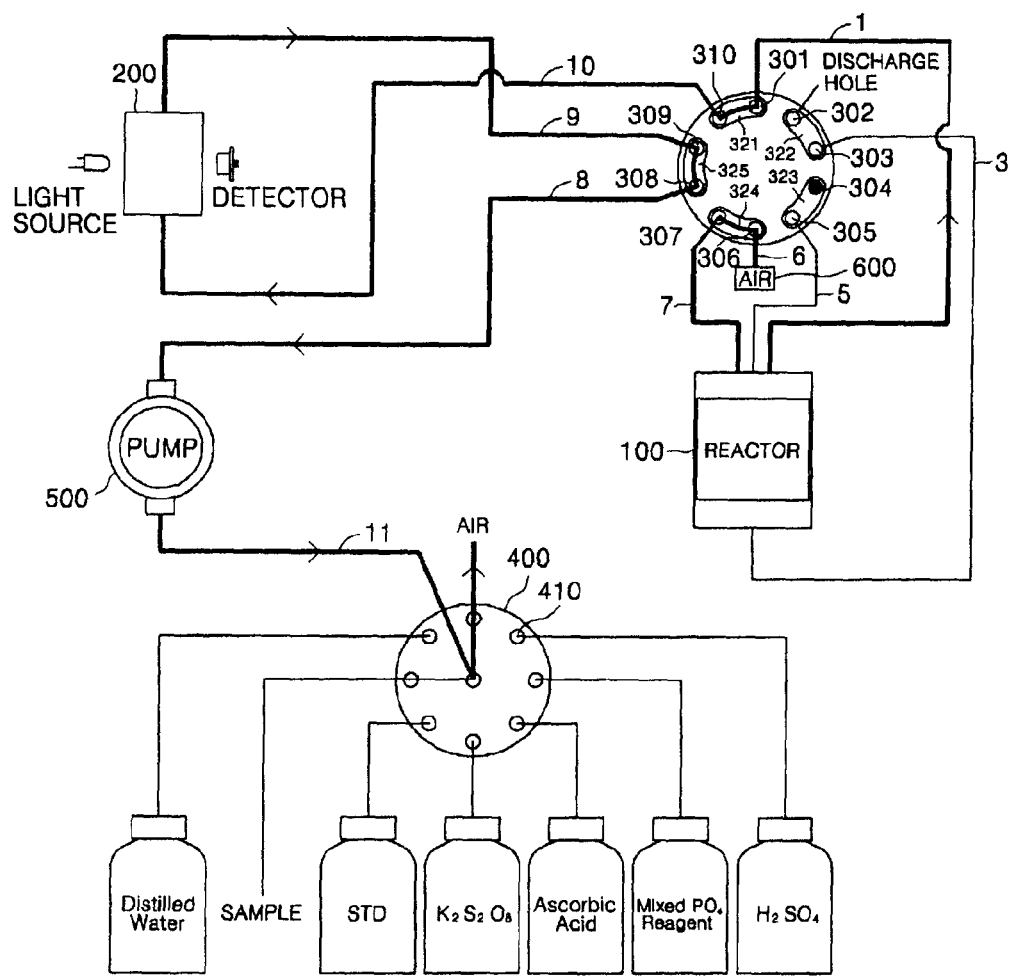
FIG. 9 is a mimetic diagram illustrating a status in which a sample and a reagent are transferred to a detector in a batch chemical analyzer according to an exemplary embodiment of the present invention.
Figure 10:
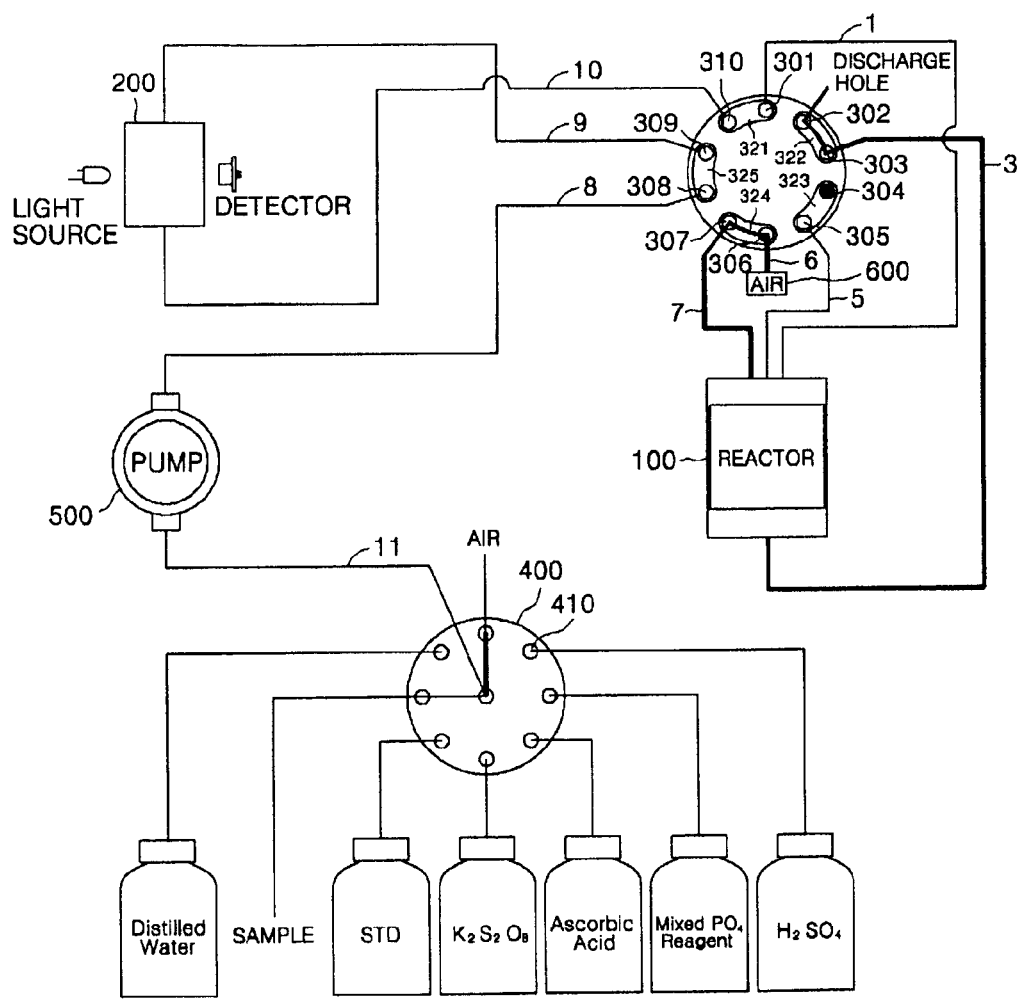
FIG. 10 is a mimetic diagram illustrating a status in which a sample and a reagent are discharged to the outside in a batch chemical analyzer according to an exemplary embodiment of the present invention.

What is claimed is:

1. A batch chemical analyzer, comprising:
a multiport valve (400 having a plurality of holes (410) radially formed and selectively connected to a plurality of sample and reagent sources; a switching valve (300);
a reaction tank (100) to mix and react the samples and reagents by receiving the sample and reagent sources from the switching valve (300);
a detector (200) to analyze the materials by detecting reaction status of the samples and reagents by receiving the sample and reagent sources from the switching valve (300);
wherein the switching valve (300) is arranged at an entrance of the reaction tank (100) and is directly connected to the reaction tank (100) and to the detector (200); and a pump (500);
wherein the pump (500) is directly connected to the multiport valve (400) and the switching valve (300) to transfer the samples and reagents to the switching valve (300) by receiving the samples and reagents from the multiport valve (400).

* * * * *